(12) United States Patent
Kaneko et al.

(10) Patent No.: US 6,555,524 B2
(45) Date of Patent: Apr. 29, 2003

(54) KETOLIDE ANTIBIOTICS

(75) Inventors: Takushi Kaneko, Guilford, CT (US); William Thomas McMillen, Indianapolis, IN (US); Wei-Guo Su, East Lyme, CT (US); Hongjuan Zhao, Waltham, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/792,937

(22) Filed: Feb. 26, 2001

(65) Prior Publication Data
US 2002/0065235 A1 May 30, 2002

Related U.S. Application Data
(60) Provisional application No. 60/186,970, filed on Mar. 6, 2000.

(51) Int. Cl.$^7$ .................... A61K 31/70; C07H 17/08
(52) U.S. Cl. .................................... 514/29; 536/7.4
(58) Field of Search ................. 536/7.4; 574/29

(56) References Cited

U.S. PATENT DOCUMENTS

| 5,747,467 A | * | 5/1998 | Agouridas et al. ............ 514/29 |
| 5,770,579 A | * | 6/1998 | Agouridas et al. ............ 514/29 |

FOREIGN PATENT DOCUMENTS

| EP | 0799833 | 10/1997 |
| EP | 0949268 | 10/1999 |
| WO | 9921871 | 5/1999 |

* cited by examiner

*Primary Examiner*—Elli Peselev
(74) *Attorney, Agent, or Firm*—Peter C. Richardson; Gregg C. Benson; Seth H. Jacobs

(57) ABSTRACT

This invention relates to compounds of the formula 1

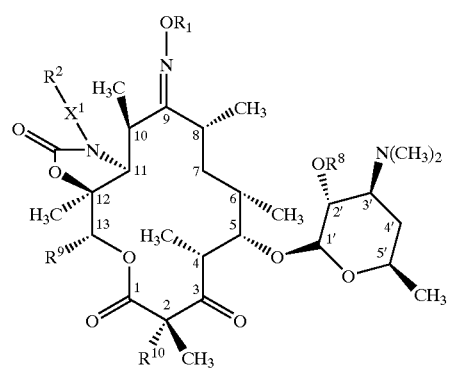

and to pharmaceutically acceptable salts, prodrugs, and solvates thereof wherein $X^1$, $R^1$, $R^2$, $R^8$, $R^9$ and $R^{10}$ are as defined herein. The compounds of formula 1 are antibacterial and antiprotozoal agents that may be used to treat various bacterial and protozoal infections and disorders related to such infections. The invention also relates to pharmaceutical compositions containing the compounds of formula 1 and to methods of treating bacterial and protozoal infections by administering the compounds of formula 1.

7 Claims, No Drawings

KETOLIDE ANTIBIOTICS

This application claims priority under 35 U.S.C. §119(e) of U.S. prov. application Ser. No. 60/186,970, filed Mar. 6, 2000, which application is hereby incorporated by reference herein.

BACKGROUND OF THE INVENTION

This invention relates to macrolide compounds that are useful as antibacterial and antiprotozoal agents in mammals, including man, as well as in fish and birds. This invention also relates to pharmaceutical compositions containing the compounds, and to methods of treating bacterial and protozoal infections by administering the compounds.

Macrolide antibiotics are known to be useful in the treatment of a broad spectrum of bacterial and protozoal infections in mammals, fish and birds. Such antibiotics include derivatives of erythromycin A such as azithromycin, which is commercially available and is referred to in U.S. Pat. No. 4,474,768, issued Oct. 2, 1984, and U.S. Pat. No. 4,517,359, issued May 14, 1985. Other macrolide antibiotics are referred to in PCT published application WO 98/56800 (published Dec. 17, 1998); U.S. Pat. No. 5,527,780, issued Jun. 18, 1996; PCT application Ser. No. PCT/IB99/01502, filed Sep. 3, 1999; United States provisional patent application Ser. No. 60/111,728 (filed Dec. 10, 1998); PCT published application WO 98/01546 (published Jan. 15, 1998); PCT published application WO 98/01571 (published Jan. 15,1998); EP published application 949268 (published Oct. 13, 1999); U.S. Pat. No. 5,747,467 (issued May 5, 1998); and United States provisional patent application Ser. No. 60/117,342, filed Jan. 27, 1999. Each of the foregoing United States patents and patent applications and EP and PCT patent applications is incorporated by reference herein in its entirety.

SUMMARY OF THE INVENTION

The present invention relates to compounds of the formula

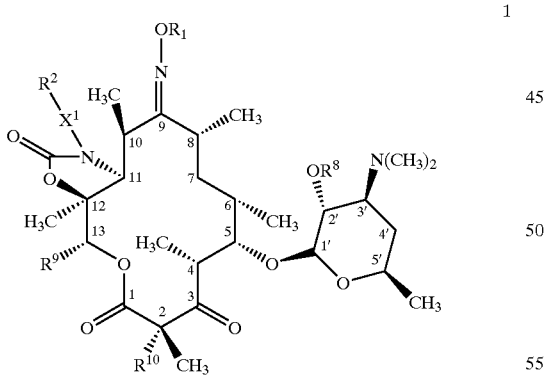

and to pharmaceutically acceptable salts, prodrugs, and solvates thereof, wherein:

$X^1$ is O, —$CR^4R^5$— or —$NR^4$—;

$R^1$ is H or $C_1$-$C_{10}$ alkyl, wherein 1 to 3 carbons of said alkyl are optionally replaced by a heteroatom selected from O, S and —N($R^4$)—, and said alkyl is optionally substituted by 1 to 3 substituents independently selected from the group consisting of —C(O)O($C_1$-$C_{10}$ alkyl), $C_1$-$C_{10}$ alkoxy, $C_1$-$C_{10}$ alkanoyl, halo, nitro, cyano, 4 to 10 membered heterocyclic, $C_1$-$C_{10}$ alkyl, —$NR^4R5^5$, $C_6$-$C_{10}$ aryl, —S(O)$_n$($C_1$-$C_{10}$ alkyl) wherein n is an integer ranging from 0 to 2, and —$SO_2NR^4R^5$;

$R^2$ is —$(CR^4R^5)_n$(4 to 10 membered heterocyclic) or —$(CR^4R^5)_n$($C_6$-$C_{10}$ aryl), wherein n is an integer from 0 to 6, and wherein from 1 to 3 $R^4$ or $R^5$ groups of the —$(CR^4R^5)_n$— moiety of the foregoing $R^2$ groups are optionally replaced with a halo substituent, and the heterocyclic and aryl moieties of the foregoing $R^2$ groups are optionally substituted with 1 to 4 $R^3$ groups;

each $R^3$ is independently selected from halo, cyano, nitro, trifluoromethoxy, trifluoromethyl, azido, hydroxy, $C_1$-$C_6$ alkoxy, $C_1$-$C_{10}$ alkyl, $C_2$-$C_6$ alkenyl, $C_2$-$C_6$ alkynyl, —$C(O)R^6$, —$C(O)OR^6$, —$OC(O)R^6$, —$NR^6C(O)R^7$, —$NR^6C(O)NR^1R^7$—$NR^6C(O)OR^7$,—$C(O)NR^6R^7$ —$NR^6R^7$, —$NR^6OR^7$, —$SO_2NR^6R^7$, —$S(O)_j$($C_1$-$C_6$ alkyl) wherein j is an integer from 0 to 0.2, —$(CR^1R^2)_t$($C_6$-$C_{10}$ aryl), —$(CR^4R^5)_t$(4 to 10 membered heterocyclic), —$(CR^4R^5)_qC(O)(CR^4R^5)_t$ ($C_6$-$C_{10}$ aryl), —$(CR^4R^5)_qC(O)(CR^4R^5)_t$(4 to 10 membered heterocyclic), —$(CR^4R^5)_tO(CR^4R^5)_q$($C_6$-$C_{10}$ aryl), —$(CR^4R^5)_tO(CR^4R^5)_q$(4 to 10 membered heterocyclic), —$(CR^4R^5)_qSO_2(CR^4R^5)_t$($C_6$-$C_{10}$ aryl), and —$(CR^4R^5)_qSO_2(CR^4R^5)_t$(4 to 10 membered heterocyclic), wherein q and t are each independently an integer from 0 to 5, 1 or 2 ring carbon atoms of the heterocyclic moieties of the foregoing $R^3$ groups are optionally substituted by an oxo (=O) moiety, and the alkyl, alkenyl, alkynyl, aryl and heterocyclic moieties of the foregoing $R^3$ groups are optionally substituted by 1 to 3 substituents independently selected from halo, cyano, nitro, trifluoromethyl, trifluoromethoxy, azido, —$OR^6$, —$C(O)R^6$, —$C(O)OR^6$, —$OC(O)R^6$, —$NR^6C(O)R^7$, —$C(O)NR^6R^7$, —$NR^6R^7$, —$NR^6OR^7$, $C_1$-$C_6$ alkyl, $C_2$-$C_6$ alkenyl, $C_2$-$C_6$ alkynyl, —$(CR^4R^5)_t$($C_6$-$C_{10}$ aryl), and —$(CR^4R^5)_t$(4 to 10 membered heterocyclic), wherein t is an integer from 0 to 5;

each $R^4$ and $R^5$ is independently selected from H and $C_1$-$C_6$ alkyl, or $R^4$ and $R^5$ taken together form a $C_3$-$C_7$ carbocyclic or 4 to 10 membered heterocyclic ring;

each $R^6$ and $R^7$ is independently selected from H, $C_1$-$C_6$ alkyl, —$(CR^4R^5)_t$($C_6$-$C_{10}$ aryl), and —$(CR^4R^5)_t$(4 to 10 membered heterocyclic), wherein t is an integer from 0 to 5, 1 or 2 ring carbon atoms of the heterocyclic group are optionally substituted by an oxo (=O) moiety, and the alkyl, aryl and heterocyclic moieties of the foregoing $R^6$ and $R^7$ groups are optionally substituted by 1 to 3 substituents independently selected from halo, cyano, nitro, —$NR^4R^5$, trifluoromethyl, trifluoromethoxy, $C_1$-$C_6$ alkyl, $C_2$-$C_6$ alkenyl, $C_2$-$C_6$ alkynyl, hydroxy, and $C_1$-$C_6$ alkoxy;

$R^8$ is H, —$C(O)(C_1$-$C_6$ alkyl), benzyl, benzyloxycarbonyl or $(C_1$-$C_6$ alkyl)$_3$silyl;

$R^9$ is H, $C_1$-$C_{10}$ alkyl; $C_2$-$C_4$ alkenyl; or $C_2$-$C_4$ alkynyl; and $R^{10}$ is selected from chloro, bromo, iodo, fluoro, and cyano.

Specific embodiments of the present invention include compounds of formula 2 (which is a specific embodiment within the genus of formula 1)

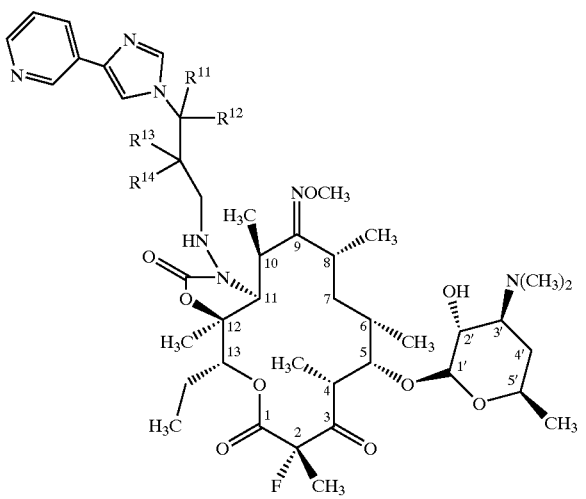

wherein $R^{11}$, $R^{12}$ $R^{13}$ and $R^{14}$ are each independently selected from H, halo, methyl and ethyl. More specific embodiments include the compounds of formula 2 wherein $R^{13}$ and $R^{14}$ are both H and $R^{11}$, and $R^{12}$ are each independently selected from H and methyl. In a preferred embodiment of the compounds of formula 2, $R^{11}$, $R^{12}$, $R^{13}$ and $R^{14}$ are each H.

The invention also relates to a pharmaceutical composition for the treatment of a bacterial infection or a protozoa infection, or a disorder related to a bacterial or protozoal infection, in a mammal, fish, or bird, which comprises a therapeutically effective amount of a compound of formula 1, or a pharmaceutically acceptable salt or solvate thereof, and a pharmaceutically acceptable carrier.

The invention also relates to a method of treating a bacterial infection or a protozoa infection, or a disorder related to a bacterial or protozoal infection, in a mammal, fish, or bird which comprises administering to said mammal, fish or bird a therapeutically effective amount of a compound of formula 1 or a pharmaceutically acceptable salt or solvate thereof.

DETAILED DESCRIPTION OF THE INVENTION

All patents, patent applications, and journal publications cited herein are hereby incorporated by reference in their entireties.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "bacterial infection(s)", "protozoal infection(s)", and "disorders related to bacterial infections or protozoal infections" include the following: pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casselflavus, S. epidermidis, S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracylines and macrolides; uncomplicated skin and soft tissue infections and abscesses, and puerperal fever related to infection by *Staphylococcus aureus*, coagulase-negative staphylococci (i.e., *S. epidermidis, S. hemolyticus*, etc.), *Streptococcus pyogenes, Streptococcus agalactiae*, Streptococcal groups C–F (minute-colony streptococci), viridans streptococci, *Corynebacterium minutissimum*, Clostridium spp., or *Bartonella henselae*; uncomplicated acute urinary tract infections related to infection by *Staphylococcus aureus*, coagulase-negative staphylococcal species, or Enterococcus spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by Cryptosporidium spp.; odontogenic infection related to infection by viridans streptococci; persistent cough related to infection by *Bordetella pertussis*; gas gangrene related to infection by *Clostridium perfringens* or Bacteroides spp.; and atherosclerosis or cardiovascular disease related to infection by *Helicobacter pylori* or *Chlamydia pneumoniae*. Bacterial infections and protozoal infections, and disorders related to such infections, which may be treated or prevented in animals include the following: bovine respiratory disease related to infection by *P. haemolytica, P. multocida, Mycoplasma bovis*, or Bordetella spp.; cow enteric disease related to infection by *E. coli* or protozoa (i.e., coccidia, cryptosporidia, etc.); dairy cow mastitis related to infection by *S. aureus, Strep. uberis, Streptococcus agalactiae, Streptococcus dysgalactiae*, Klebsiella spp., Corynebacterium, or Enterococcus spp.; swine respiratory disease related to infection by *A. pleuro., P. multocida*, or Mycoplasma spp.; swine enteric disease related to infection by *E. coli, Lawsonia intracellularis*, Salmonella, or *Serpulina hyodysinteriae*; cow footrot related to infection by Fusobacterium spp.; cow metritis related to infection by *E coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *S. epidermidis, S.*

*intermedius*, coagulase neg. Staphylococcus or *P. multocida*; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoal infections, and disorders related to such infections, which may be treated or prevented in accord with the method of the present invention are referred to in J. P. Sanford et al., "The Sanford Guide To Antimicrobial Therapy," 26 th Edition, (Antimicrobial Therapy, Inc., 1996).

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having cyclic, straight and/or branched moieties. It is to be understood that to include cyclic moieties, the alkyl group must include at least 3 carbon atoms.

The term "alkenyl", as used herein, unless otherwise indicated, includes alkyl groups as defined above having at least one carbon—carbon double bond at some point in the alkyl chain.

The term "alkynyl", as used herein, unless otherwise indicated, includes alkyl groups as defined above having at least one carbon—carbon triple bond at some point in the alkyl chain.

The term "aryl", as used herein, unless otherwise indicated, includes an organic radical derived from an aromatic hydrocarbon by removal of one hydrogen, such as phenyl or naphthyl.

The term "4 to 10 membered heterocyclic", as used herein, unless otherwise indicated, includes aromatic and non-aromatic heterocyclic groups containing one or more heteroatoms each selected from O, S and N, wherein each heterocyclic group has from 4 to 10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl. benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of formula 1. The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodode, and valerate salts.

Those compounds of the formula 1 that are acidic in nature, are capable of forming base salts with various pharmacologically acceptable cations. Examples of such salts include the alkali metal or alkaline earth metal salts and particularly, the sodium and potassium salts.

Certain compounds of formula 1 may have asymmetric centers and therefore exist in different enantiomeric forms. This invention relates to the use of all optical isomers and stereoisomers of the compounds of formula 1 and mixtures thereof. In particular, the invention includes both the E and Z isomers of the —$OR^1$ group connected to the nitrogen of the oxime moiety at C-9 of the macrolide ring of formula 1.

The invention includes tautomers of the compounds of formula 1.

The present invention also includes isotopically-labelled compounds, and the pharmaceutically acceptable salts thereof, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e, $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing, and methods of treating bacterial infections through administering, prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

The preparation of the compounds of the present invention is illustrated in the following Schemes.

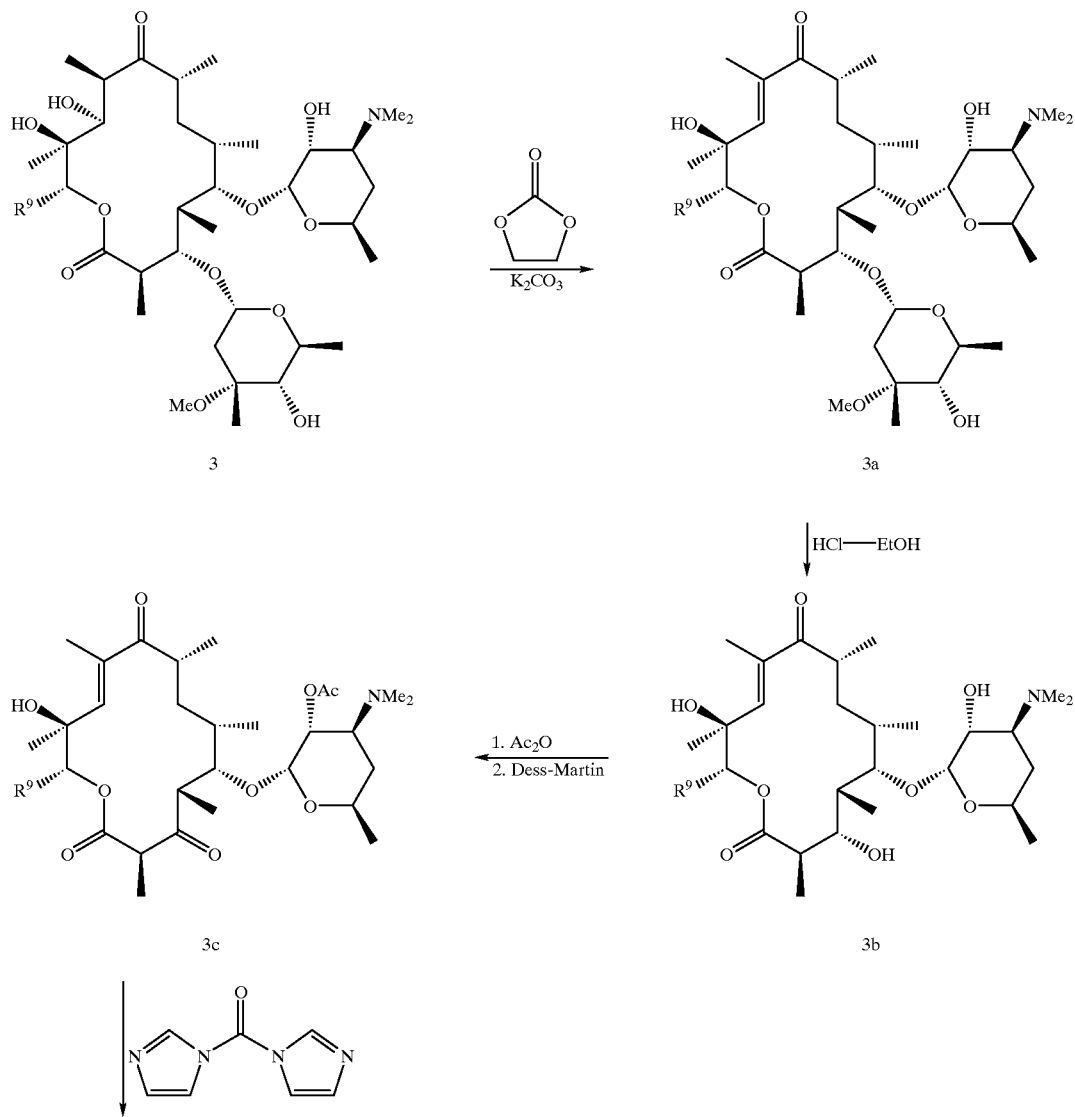

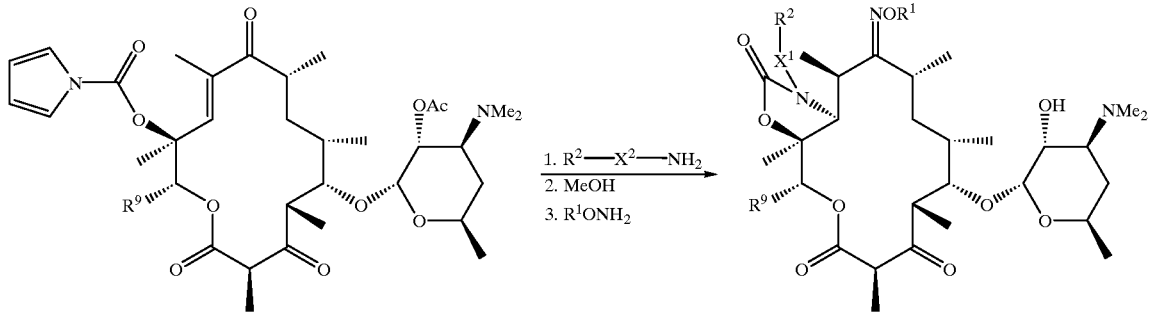

The preparation of compounds of formula 4 follows the scheme above. The 6-deoxy erythromycin A 3 is treated with ethylene carbonate in toluene in the presence of a base, such as potassium carbonate at 100 to 110° C. The resultant allylic alcohol 3a is converted to C-3 alcohol 3b by treatment with 2 N hydrochloric acid in ethanol. This diol 3b is selectively oxidized with Dess-Martin reagent to give C-3 keto derivative 3c. The C-11,12-cyclic carbamate is installed using a conventional method by the chemical sequence: (1) treatment of the allylic alcohol 3c with carbonyl diimidazole in the presence of potassium carbonate to form the acyl imidazole intermediate 3d, and (2) treatment of 3d with an amine or hydrazine in a polar solvent, such as acetonitrile at 40 to 80° C. to provide the final product 4.

Starting materials and/or final compounds of formula 1 wherein $R^9$ is a moiety other than ethyl within the definition of $R^9$ provided above may be prepared as described in PCT published applications WO 98/01571, published Jan. 15, 1998, and WO 98/01546, published Jan. 15, 1998. Other specific methods that relate to the synthesis of the compounds of the present invention are referred to in PCT patent application publication number WO 98/38199 (published Sep. 3, 1998), PCT patent application publication number WO 98/56800 (published Dec. 17, 1998), United States provisional patent application Ser. No. 60/101,263 (filed Sep. 22, 1998) and counterpart PCT application serial no. PCT/IB99/01502, filed Sep. 3, 1999, United States provisional patent application Ser. No. 60/111,728 (filed Dec. 10, 1998), European patent application EP 487,411, and European patent application EP 799,833. In the above Schemes, all substituents are as defined for formula 1 referred to above except where otherwise indicated.

The starting materials may require proper functional group protection before various modifications can take place, and deprotection after desired modifications are complete. Hydroxyl groups are generally protected as acetates, Cbz carbonates or with a trialklylsilyl group. The C-2' hydroxyl group is a potentially reactive hydroxyl group among the numerous hydroxyl groups present in macrolide compounds of the type claimed herein. The C-2' hydroxyl group is selectively protected by treating the compound with one equivalent of acetic anhydride in dichloromethane in the absence of external base. This process selectively converts the C-2' hydroxyl group into the corresponding acetate. The hydroxyl protecting group can be removed by treating the compound with methanol at a temperature ranging from about 0° C. to 40° C. to about 65° C. for 10 to 48 hours. Other methods of selective protection and deprotection are familiar to those skilled in the art. As noted in formula 1, the compounds of the invention include such protected compounds, e.g., where $R^8$ is other than H.

With reference to the scheme below, the compound of formula 5, wherein $R^{10}$ is a halo group and all other substituents are as defined above, may be prepared by treating the compound of formula 4 by the sequence: (1) C-2' protection, such as acetylation with acetic anhydride, (2) treatment with a base, such as sodium hydride, potassium hydride, potassium hexamethyldisilazide (KHMDS), pyridine, sodium carbonate, or lithium diisopropylamide, preferably KHMDS, and a halogenating agent, such as N-fluorobenzensulfoimide, SELECTFLUOR™ (marketed by Air Products and Chemicals, Inc., Allentown, Pa., United States of America) for fluorination, pyridinium tribromide or cyanogen bromide for bromination, or hexachloroethane for chlorination, in a solvent, such as in N,N-dimethylformamide (DMF), tetrahydrofuran (THF), $CH_2Cl_2$, or N-methylpyrrolidone, or a mixture of the foregoing solvents, preferably DMF. The reaction temperature, which is highly dependent on the reagent used, can be from −78° C. to 60° C., and (3) C-2' deprotection to give the compound of formula 6 by treatment with methanol. The compound of formula 6 corresponds to the compound of formula 1 wherein $R^8$ is H.

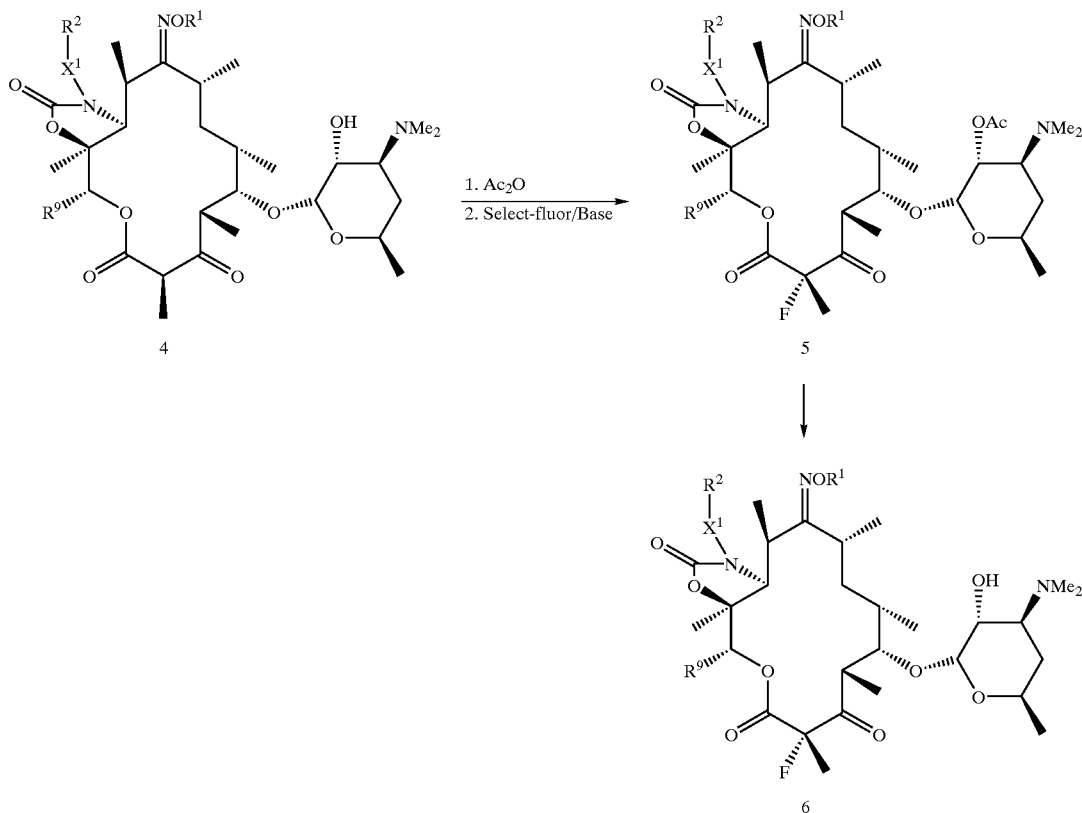

The compounds of the present invention may have asymmetric carbon atoms. Diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers, are considered as part of the invention.

Any compounds of formula 1 that are basic in nature are capable of forming a wide variety of salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Any compounds of the formula 1 that are acidic in nature are capable of forming base salts with various pharmacologically acceptable cations. Examples of such salts include the alkali metal or alkaline-earth metal salts and particularly, the sodium and potassium salts. These salts may be prepared by conventional techniques. The chemical bases which are used as reagents to prepare the pharmaceutically acceptable base salts of this invention are those which form non-toxic base salts with any acidic compounds of formula 1. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The activity of a compound of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to assay the ability of compounds to act against pathogenic bacterial strains, and especially macrolide resistant strains. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and the ability to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally preventing binding by all three antibiotic classes. Two types of macrolide efflux genes have been described: msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The pathogenic strains used in this assay may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562-2566 (1996). The assay is performed in microtiter trays and interpreted according to *Performance Standards for Antimicrobial Disk Susceptibility Tests-Sixth Edition: Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as 40 mg/ml stock solutions.

| Strain Designation | Macrolide Resistance Mechanism(s) |
|---|---|
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | ermB |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Streptococcus pneumoniae* 0085 | susceptible |
| *Haemophilus influenzae* 0131 | susceptible |
| *Moraxella catarrhalis* 0040 | susceptible |
| *Moraxella catarrhalis* 1055 | erythromycin intermediate resistance |
| *Escherichia coli* 0266 | susceptible |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compound is prepared by solubilizing 1 mg of the compound in 125 $\mu$l of dimethylsulfoxide (DMSO). Dilutions of the test compound are prepared using uninoculated BHI broth. The concentrations of the test compound used range from 200 $\mu$g/ml to 0.098 $\mu$g/ml by two-fold serial dilutions. The *P. multocida* inoculated BHI is diluted with uninoculated BHI broth to make a $10^4$ cell suspension per 200 $\mu$l. BHI cell suspensions are mixed with respective serial dilutions of the test compound, and incubated at 37° C for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five *P. haemolytica* colonies isolated from an agar plate are inoculated into BHI broth and incubated overnight at 37° C. with shaking (200 rpm). The next morning, 300 $\mu$l of the fully grown *P. haemolytica* preculture is inoculated into 3 ml of fresh BHI broth and incubated at 37° C. with shaking (200 rpm). The appropriate amounts of the test compounds are dissolved in ethanol and a series of two-fold serial dilutions prepared. Two ml of the respective serial dilution is mixed with 18 ml of molten BHI agar and solidified. When the inoculated P. haemolytica culture reaches 0.5 McFarland standard density, about 5 $\mu$l of the culture is inoculated onto BHI agar plates containing the various concentrations of the test compound using a Steers Replicator and incubated for 18 hours at 37° C. Initial concentrations of the test compound range from 100–200 $\mu$g/ml. The MIC is equal to the concentration of the test compound exhibiting 100% inhibition of growth of *P. haemolytica* as determined by comparison with an uninoculated control.

The in vivo activity of the compounds of formula 1 can be determined by conventional animal protection studies well known to those skilled in the art, usually carried out in mice. A description of an example of such a study follows.

Mice are allotted to cages (10 per cage), and allowed to acclimate for a minimum of 48 hours before being used. Animals are inoculated with 0.5 ml of a $3 \times 10^3$ CFU/ml bacterial suspension (*P. multocida* strain 59A006) intraperitoneally. Each experiment has at least 3 non-medicated control groups, including one infected with 0.1×challenge dose and two infected with 1×challenge dose; a 10×challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. Administration is normally carried out orally or subcutaneously. Subcutaneous doses are administered into the loose skin in the back of the neck whereas oral doses are given by means of a feeding needle. In both cases, a volume of 0.2 ml is used per mouse. Compounds are administered at 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to a bacterial infection which would be lethal in the absence of compound.

The compounds of formula 1, and the pharmaceutically acceptable salts and solvates thereof (hereinafter "the active compounds"), may be administered through oral, parenteral, topical, or rectal routes in the treatment or prevention of bacterial or protozoa infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato, or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The present invention is illustrated by the following examples, which are intended to exemplify, and not limit, the scope of the invention.

EXAMPLE 1

To a round-bottomed flask equipped with a Dean-Stock water removal apparatus were placed 6-deoxy erythromycin A (718 mg, 1 mmol), ethylene carbonate (8.5 mmol) and potassium carbonate (5 mmol) and benzene (20 ml). The mixture was heated at reflux for 3.5 hours. After cooling, the mixture was decanted, diluted with ethyl acetate, and washed with water and saturated sodium chloride. Drying over Magnesium sulfate and evaporation to dryness gave the corresponding 10,11-dehydro product (602 mg, 86%; Mass Spec: 701, M+H$^+$).

EXAMPLE 2

The product of the Example 1 (600 mg, 0.86 mmol) was dissolved in ethanol (1 ml) and treated with 2 N aqueous HCl (1 ml) at room temperature for 16 hours. The reaction was made basic with 5 M sodium hydroxide and extracted with dichloromethane (3×20 ml). Drying over potassium carbonate, evaporation and purification by silica gel chromatography using 4% methanol-methylene chloride containing 0.3% concentrated ammonium hydroxide afforded the corresponding C-3 alcohol as a white foam (311 mg, 67%; Mass Spec: 542, M+H$^+$).

EXAMPLE 3

The product of Example 2 (300 mg, 0.55 mmol) was dissolved in dichloromethane (5 ml) and treated with acetic anhydride (1.05 equiv.). The resulting mixture was stirred at room temperature for 16 hours before water was introduced. The reaction mixture was poured into 5% aqueous sodium carbonate solution (20 ml) and extracted with dichloromethane (3×20 ml). The combined organic phase was washed with brine, dried over potassium carbonate and concentrated in vacuo. Purification by silica gel chromatography using 3% methanol in dichloromethane containing 0.3% concentrated ammonium hydroxide gave rise to the corresponding 2"-acetate (323 mg, 100%; Mass Spec: 584 M+H$^+$).

EXAMPLE 4

The alcohol obtained in Example 3 (323 mg, 0.55 mmol) was dissolved In dichloromethane (5 ml). Dess-Martin reagent (1.5 equiv.) was added and the resulting mixture stirred at room temperature for 2 hours before 5% sodium carbonate was introduced. After stirring for 15 min., the layers were separated and the aqueous phase extracted with dichloromethane (3×20 ml). The combined organics were washed with brine, dried over potassium carbonate and concentrated to provide the corresponding C-3 ketone (320 mg, 100%, Mass Spec: 583 M+H$^+$).

EXAMPLE 5

The product of Example 4 (320 mg, 0.55 mmol) was dissolved in dichloromethane (5 ml). To it were added N,N'-carbonyl diimidazole (5 equiv.) and potassium carbonate (3 equiv.). The resulting reaction mixture was stirred at room temperature for 16 hours before water was added. After stirring for 15 min, the layers were separated, and the aqueous phase extracted with dichloromethane (3×20 ml). The combined organic phase was washed with brine, dried over potassium carbonate and concentrated to dryness to produce the corresponding 12-acyl imidazole derivative (370 mg, 100%; Mass Spec: 676 M+H$^+$).

EXAMPLE 6

The product of Example 5 (370 mg, 0.55 mmol) was dissolved in acetonitrile (5 ml) and then hydrazine monohydrate added (5 equiv.). The reaction was heated at reflux for 12 hours. After cooling to room temperature, the mixture was poured into 5% sodium carbonate and extracted with dichloromethane (3×20 ml). Combined extracts were washed with brine, dried over potassium carbonate, concentrated in vacuo and purified by silica gel chromatography using 5% methanol in dichloromethane containing 0.4% concentrated ammonium hydroxide to give the corresponding 11,12-cyclic carbazate (220 mg, 67%; Mass Spec: 598, M+H$^+$).

EXAMPLE 7

The product of Example 6 (220 mg, 0.37 mmol) was dissolved in ethanol (3 ml) and benzyloxyamine hydrochloride (10 equiv.) added. After refluxing for 6 hours, the mixture was cooled to room temperature and water introduced. The pH was adjusted to 9 by addition of 1 N sodium hydroxide. The mixture was extracted with dichloromethane (3×20 ml) and combined extracts washed with brine. Drying over potassium carbonate, evaporation of solvent and purification by silica gel chromatography using 5% methanol in dichloromethane containing 0.3% concentrated ammonium hydroxide afforded the corresponding C-9 benzyloxime (129 mg, 55%; Mass Spec: 703 M+H$^+$).

EXAMPLE 8

Following the procedure described in Example 7 and using methoxylamine the corresponding C-9 methoxime was prepared in 35% yield (Mass Spec: 728 (M+H$^+$).

EXAMPLE 9

The product of Example 7 (120 mg, 0.17 mmol) was dissolved in acetic acid and acetonitrile (5:1 ratio, 1 ml). To it were added 3-quinolin-4-yl-propyl aldehyde (1.2 equiv.) and sodium cyanoborohydride (1.2 equiv.). After stirring at room temperature for 0.5 hours, water was added and the mixture stirred for 20 min. Extraction with dichloromethane (3×20 ml), washing of extracts with brine, drying over potassium carbonate, concentration and silica gel purification using 5% methanol in dichloromethane containing 0.3% concentrated ammonium hydroxide produced the corresponding N-alkylated product (98 mg, 66%; Mass Spec: 873 M+H$^+$).

EXAMPLE 10

Following the procedure described in Example 9 and using the product of Example 8, the corresponding C-9 methoxime was prepared in 50% yield (Mass Spec: 796 (M+H$^+$).

EXAMPLE 11

Following the procedure described in Example 9 and using the product of Example 6, the corresponding C-9 ketone was prepared in 88% yield.

EXAMPLE 12

The product of Example 11 (100 mg, 0.13 mmol) was dissolved in dichloromethane and treated with acetic anhydride (1.05 equiv.) at room temperature for 12 hours. The resulting reaction mixture was poured into 5% sodium carbonate and extracted with dichloromethane (3×20 ml). Combined extracts were washed with brine, dried over potassium carbonate and concentrated to dryness to provide the corresponding 2' acetate (105 mg, 100%; Mass Spec: 810, M+H$^+$).

EXAMPLE 13

The product of Example 12 (105 mg, 0.13 mmol) was dissolved in DMF, cooled to —50° C. To it were added sequentially sodium hydride (2 equiv., 60% in oil) and SelectFluor (1.05 equiv.). After two hours, water was added and the reaction was allowed to warm to room temperature. The mixture was poured into 5% sodium carbonate, and extracted with ethyl acetate (3×20 ml). Combined extracts were washed with water and brine, dried over sodium sulfate, concentrated and purified by silica gel chromatography using 5% methanol in dichloromethane containing 0.3% concentrated ammonium hydroxide to give the corresponding C-2 fluoro derivative (92 mg, 86%; Mass Spec: 828, M+H$^+$).

EXAMPLE 14

The product of Example 13 (92 mg, 0.11 mmol) was dissolved in methanol and let stand for 16 hours. Concentration gave the corresponding 2'-alcohol (87 mg, 100%; Mass Spec: 786 M+H$^+$).

What is claimed is:
1. A compound of the formula

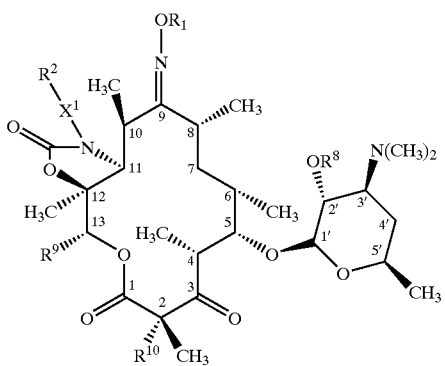

1 or a pharmaceutically acceptable salt, prodrug, or solvate thereof, wherein:

$X^1$ is O, —CR$^4$R$^5$— or —NR$^4$—;

$R^1$ is H or C$_1$-C$_{10}$ alkyl, wherein 1 to 3 carbons of said alkyl are optionally replaced by a heteroatom selected from a group consisting of O, S and —N(R$^4$)—, and said alkyl is optionally substituted by 1 to 3 substituents independently selected from the group consisting of —C(O)O(C$_1$-C$_{10}$ alkyl), C$_1$-C$_{10}$ alkoxy, C$_1$-C$_{10}$ alkanoyl, halo, nitro, cyano, 4 to 10 membered heterocyclyl, C$_1$-C$_{10}$ alkyl, —NR$^4$R5$^5$, C$_6$-C$_{10}$ aryl, —S(O)$_n$(C$_1$-C$_{10}$ alkyl) wherein n is an integer ranging from 0 to 2, and —SO$_2$NR$^4$R$^5$;

$R^2$ is —(CR$^4$R$^5$)$_n$(4 to 10 membered heterocyclic) or —(CR$^4$R$^5$)$_n$(C$_6$-C$_{10}$aryl), wherein n is an integer from 0 to 6, and wherein from 1 to 3 R$^4$ or R$^5$ groups of the —(CR$^4$R$^5$)$_n$— moiety of the foregoing R$^2$ groups are optionally replaced with a halo substituent, and the heterocyclic and aryl moieties of the foregoing R$^2$ groups are optionally substituted with 1 to 4 R$^3$ groups;

each R$^3$ is independently selected from halo, cyano, nitro, trifluoromethoxy, trifluoromethyl, azido, hydroxy, C$_1$-C$_6$ alkoxy, C$_1$-C$_{10}$ alkyl, C$_2$-C$_6$ alkenyl, C$_2$-C$_6$ alkynyl, —C(O)R$^6$, —C(O)OR$^6$, —OC(O)R$^6$, —NR$^6$C(O)R$^7$, —NR$^6$C(O)NR$^1$R$^7$, —NR$^6$C(O)OR$^7$, —C(O)NR$^6$R$^7$, —NR$^6$R$^7$, —NR$^6$OR$^7$, —SO$_2$NR$^6$R$^7$, —S(O)$_j$(C$_1$-C$_6$ alkyl) wherein j is an integer from 0 to 2, —(CR$^1$R$^2$)$_t$(C$_6$-C$_{10}$ aryl), —(CR$^4$R$^5$)$_t$(4 to 10 membered heterocyclic), —(CR$^4$R$^5$)$_q$C(O) (CR$^4$R$^5$)$_t$(C$_6$-C$_{10}$ aryl), —(CR$^4$R$^5$)$_q$C(O) (CR$^4$R$^5$)$_t$(4 to 10 membered heterocyclic), —(CR$^4$R$^5$)$_t$O(CR$^4$R$^5$)$_q$(C$_6$-C$_{10}$ aryl), —(CR$^4$R$^5$)$_t$O(CR$^4$R$^5$)$_q$(4 to 10 membered heterocyclic), —(CR$^4$R$^5$)$_q$SO$_2$(CR$^4$R$^5$)$_t$(C$_6$-C$_{10}$ aryl), and —(CR$^4$R$^5$)$_q$SO$_2$(CR$^4$R$^5$)$_t$(4 to 10 membered heterocyclic), wherein q and t are each independently an integer from 0 to 5, 1 or 2 ring carbon atoms of the heterocyclic moieties of the foregoing R$^3$ groups are optionally substituted by an oxo (=O) moiety, and the alkyl, alkenyl, alkynyl, aryl and heterocyclic moieties of the foregoing R$^3$ groups are optionally substituted by 1 to 3 substituents independently selected from the group consisting of halo, cyano, nitro, trifluoromethyl, trifluoromethoxy, azido, —OR$^6$, —C(O)R$^6$, —C(O)OR$^6$, —OC(O)R$^6$, —NR$^6$C(O)R$^7$, —C(O)NR$^6$R$^7$, —NR$^6$R$^7$, —NR$^6$OR$^7$, C$_1$-C$_6$ alkyl, C$_2$-C$_6$ alkenyl, C$_2$-C$_6$ alkynyl, —(CR$^4$R$^5$)$_t$(C$_6$-C$_{10}$ aryl), and —(CR$^4$R$^5$)$_t$(4 to 10 membered heterocyclic), wherein t is an integer from 0 to 5;

each R$^4$ and R$^5$ is independently selected from the group consisting of H and C$_1$-C$_6$ alkyl;

each R$^6$ and R$^7$ is independently selected the group consisting of from H, C$_1$-C$_6$ alkyl, —(CR$^4$R$^5$)$_t$(C$_6$-C$_{10}$ aryl), and —(CR$^4$R$^5$)$_t$(4 to 10 membered heterocyclic), wherein t is an integer from 0 to 5, 1 or 2 ring carbon atoms of the heterocyclic group are optionally substituted by an oxo (=O) moiety, and the alkyl, aryl and heterocyclic moieties of the foregoing R$^6$ and R$^7$ groups are optionally substituted by 1 to 3 substituents independently selected the group consisting of from halo, cyano, nitro, —NR$^4$R$^5$, trifluoromethyl, trifluoromethoxy, C$_1$-C$_6$ alkyl, C$_2$-C$_6$ alkenyl, C$_2$-C$_6$ alkynyl, hydroxy, and C$_1$-C$_6$ alkoxy;

R$^8$ is H, —C(O) (C$_1$-C$_6$ alkyl), benzyl, benzyloxycarbonyl or (C$_1$-C$_6$ alkyl)$_3$ silyl;

R$^9$ is H, C$_1$-C$_{10}$ alkyl; C$_2$-C$_4$ alkenyl; or C$_2$-C$_4$ alkynyl; and R$^{10}$ is selected from the group consisting of from chloro, bromo, iodo, fluoro, and cyano.

2. A compound of the formula

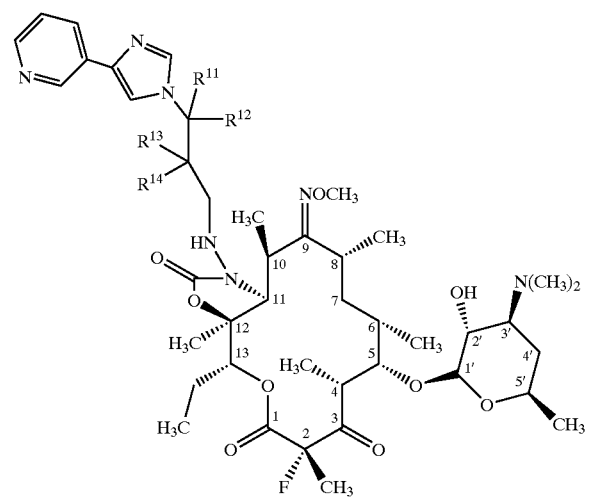

2 or a pharmaceutically acceptable salt, prodrug, or solvate thereof, wherein R$^{11}$, R$^{12}$, R$^{13}$ and R$^{14}$ are each independently selected from the group consisting of H, halo, methyl and ethyl.

3. A compound according to claim 2 wherein R$^{13}$ and R$^{14}$ are both H and R$^{11}$ and R$^{12}$ are each independently selected from the group consisting of H and methyl.

4. A compound according to claim 2 wherein R$^{11}$, R$^{12}$, R$^{13}$ and R$^{14}$ are each H.

5. A pharmaceutical composition for the treatment of a a bacterial infection or a protozoal infection in a mammal, fish, or bird which comprises a therapeutically effective amount of a compound of claim 1 and a pharmaceutically acceptable carrier.

6. A method of treating a bacterial infection or a protozoal infection in a mammal, fish, or bird which comprises administering to said mammal, fish or bird a therapeutically effective amount of a compound of claim 1.

7. A method of preparing a compound according to claim 1 wherein $R^{10}$ is chloro, bromo, iodo, or fluoro, which comprises treating a compound of the formula

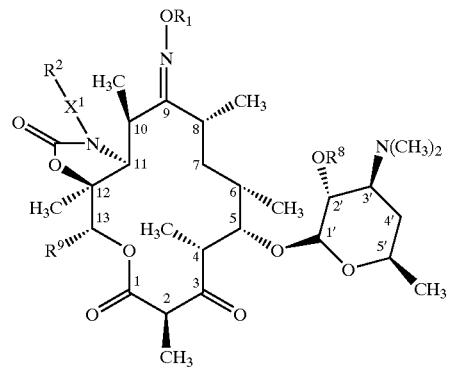

with a halogenating agent.

* * * * *